(12) United States Patent
Chen

(10) Patent No.: US 9,285,349 B2
(45) Date of Patent: Mar. 15, 2016

(54) ANALYTE DETECTORS AND METHODS FOR THEIR PREPARATION AND USE

(71) Applicant: EMPIRE TECHNOLOGY DEVELOPMENT LLC, Wilmington, DE (US)

(72) Inventor: Qingyue Chen, Beijing (CN)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/441,396

(22) PCT Filed: Nov. 7, 2012

(86) PCT No.: PCT/CN2012/084213
§ 371 (c)(1),
(2) Date: May 7, 2015

(87) PCT Pub. No.: WO2014/071566
PCT Pub. Date: May 15, 2014

(65) Prior Publication Data
US 2015/0308995 A1    Oct. 29, 2015

(51) Int. Cl.
*G01N 15/06* (2006.01)
*G01N 33/00* (2006.01)
(Continued)

(52) U.S. Cl.
CPC ............ *G01N 31/223* (2013.01); *G01N 27/125* (2013.01); *G01N 33/0004* (2013.01)

(58) Field of Classification Search
CPC ........ G01N 15/06; G01N 33/00; G01N 33/48
USPC .......... 422/68.1, 82.01, 82.02, 83, 98; 436/43, 436/140; 977/700, 957, 723, 773, 779, 953
See application file for complete search history.

(56) References Cited

U.S. PATENT DOCUMENTS 3,530,002 A    9/1970  Little
3,924,219 A   12/1975  Braun
(Continued)

FOREIGN PATENT DOCUMENTS

CN    101144789 A    3/2008
CN    101419181 A    4/2009
(Continued)

OTHER PUBLICATIONS

International Search Report and Written Opinion for International Application No. PCT/CN2012/084213 mailed Aug. 15, 2013.
(Continued)

*Primary Examiner* — Brian J Sines
(74) *Attorney, Agent, or Firm* — Pepper Hamilton LLP

(57) ABSTRACT

Embodiments described herein provide for gas detectors and methods for their preparation and use. Some embodiments provide for a gas detection film including an insulating base layer, a conducting layer including a plurality of conductive clusters having a known degree of percolation below a percolation threshold; and a non-conductive reactant layer between the insulating base layer and the conducting layer. Some embodiments described in this document also provide for methods of making a gas detection film, methods of detecting a detectable gas, and kit for detecting a detectable gas. In some embodiments, the detectable gas may include mercury vapor, water vapor, formaldehyde or a combination thereof.

22 Claims, 3 Drawing Sheets

(51) Int. Cl.
*G01N 33/48* (2006.01)
*G01N 31/22* (2006.01)
*G01N 27/12* (2006.01)

(56) References Cited

U.S. PATENT DOCUMENTS

| | | | |
|---|---|---|---|
| 4,185,143 | A | 1/1980 | Birt et al. |
| 5,424,147 | A | 6/1995 | Khasin et al. |
| 6,033,602 | A | 3/2000 | Sunshine et al. |
| 7,070,882 | B1 | 7/2006 | Ferrando |
| 7,389,671 | B1 | 6/2008 | Xu et al. |
| 7,494,907 | B2 | 2/2009 | Brown et al. |
| 8,872,615 | B2 * | 10/2014 | Kennedy et al. ............ 338/32 R |
| 2004/0099047 | A1 | 5/2004 | Raisanen |
| 2004/0129570 | A1 * | 7/2004 | Talin et al. ................... 205/109 |
| 2005/0200272 | A1 * | 9/2005 | Shimoyama et al. ......... 313/503 |
| 2006/0063296 | A1 * | 3/2006 | Park et al. ...................... 438/93 |
| 2007/0132043 | A1 | 6/2007 | Bradley et al. |
| 2008/0307856 | A1 | 12/2008 | Chen et al. |
| 2009/0117513 | A1 | 5/2009 | Nameh et al. |
| 2009/0311567 | A1 | 12/2009 | Visco et al. |
| 2011/0269007 | A1 | 11/2011 | Visco et al. |

FOREIGN PATENT DOCUMENTS

| | | |
|---|---|---|
| CN | 101862505 A | 10/2010 |
| EP | 1615280 A1 | 1/2006 |
| JP | 2007107047 A | 4/2007 |

OTHER PUBLICATIONS

International Search Report and Written Opinion for International Application No. PCT/CN2012/084227 mailed Aug. 15, 2013.
International Search Report and Written Opinion for counterpart application PCT/CN2012/084223 dated Aug. 15, 2013.
DWD Sensorbased Singlezone Water Leak Detector, accessed at http://web.archive.org/web/20121010082630/http://www.wayscale.com/water-leak-detection/domestic-sensor-based-single-zone/dwd-water-leak-detector, accessed on May 7, 2015 pp. 1-2.
Global Footwear Market to Reach US$195 Billion by 2015, According to New Report by Global Industry Analysts, Inc., accessed at http://web.archive.org/web/20140620010106/http://www.prweb.com/releases/footwear_athletic/outdoor_casual_formal/prweb8058110.htm, accessed on Jan. 12, 2011, pp. 1-2.
Percolation Theory, accessed at https://web.archive.org/web/20120813175019/http://ciks.cbt.nist.gov/garbocz/paper22/node4.html, accessed on May 1, 2015, p. 1.
Phillips, Swimming with sensors, *RSC Advancing the Chemical Sciences*, accessed at http://web.archive.org/web/20121021032229/http://www.rsc.org/chemistryworld/News/2011/June/02061101.asp, accessed on Jun. 2, 2011, pp. 1-2.
Water and Flood Sensors, accessed at http://web.archive.org/web/20141103182847/http://www.homesecuritystore.com/safety/water-flood-sensors, accessed on May 7, 2015, pp. 1-4.

* cited by examiner

ANALYTE DETECTORS AND METHODS FOR THEIR PREPARATION AND USE

CLAIM OF PRIORITY

This application is a national phase application under 35 U.S.C. §371 of International Application No. PCT/CN2012/084213, filed Nov. 7, 2012 and entitled "GAS DETECTORS AND METHODS FOR THEIR PREPARATION AND USE," the disclosure of which is incorporated by reference in its entirety and for all purposes.

A. BACKGROUND

Gases and vapors which may be potentially hazardous, contaminative, dangerous or otherwise undesirable, such as propane, water vapor, formaldehyde, methane, carbon monoxide, mercury vapor, ethylene oxide, hydrogen sulfide, and other hazardous gases, are sometimes difficult to detect, especially where they are odorless or present at levels that cannot be smelled, or are masked by other odors. The danger of these hazardous gases is becoming increasingly apparent, especially in industrial plants, mines, environmentally sealed homes and office buildings, recreational and other vehicles and other environments in which people are present for long periods of time. To detect and quantify the concentration of gases, various sensors have been developed which typically include visual detection of color change or measurement of electric properties. However, such sensors require a long reaction time and have low sensitivity. Such hazards are also found in liquid streams.

Furthermore, the existing portable devices for detecting gases such as mercury vapor, water vapor, and formaldehyde are expensive. Accordingly, there is a need for a detection apparatus for sensing and measuring these gases that is easy to fabricate, cost efficient and reliable.

B. SUMMARY

Embodiments described in this document relate to analyte detectors, in some embodiments gas detectors, and methods for their preparation and use. Some embodiments provide for a gas detection film including an insulating base layer, a conducting layer including a plurality of conductive clusters having a known degree of percolation below a percolation threshold; and a non-conductive reactant layer between the insulating base layer and the conducting layer. In some embodiments, the detectable gas may include mercury vapor, water vapor, formaldehyde or a combination thereof.

Some embodiments provide for a gas detection apparatus including a gas detection film including an insulating base layer, a conducting layer including a plurality of conductive clusters having a known degree of percolation below a percolation threshold; and a non-conductive reactant layer between the insulating base layer and the conducting layer. In some embodiments, the detectable gas may include mercury vapor, water vapor, formaldehyde or a combination thereof.

Some embodiments provide for a method of preparing a gas detection film including the steps of providing an insulating base layer; depositing onto the insulating base layer a non-conductive reactant layer that is capable of reacting with a detectable gas to increase conductivity of the gas detection film; depositing onto the non-conductive reactant layer a conducting layer having a known degree of percolation below a percolation threshold.

Some embodiments relate to a method of detecting a detectable gas, the method encompassing the steps of providing a gas stream suspected of containing the detectable gas; providing a gas film having an insulating base layer, a conducting layer including a plurality of conducting clusters having a known degree of percolation that is below a percolation threshold, and a non-conductive reactant layer between the insulating base layer and the conducting layer; exposing the gas detection film to the gas stream; and measuring a conductance of the gas detection film, wherein an increase in conductance of the gas detection film from a baseline level indicates the presence of the detectable gas.

Some embodiments relate to a kit for detecting a detectable gas including a gas detection film having an insulating base layer; a conducting layer including a plurality of conducting clusters having a known degree of percolation that is below a percolation threshold; and a non-conductive reactant layer between the insulating base layer and the conducting layer; instructions on how to use the gas detection film.

C. BRIEF DESCRIPTION OF THE FIGURES

The accompanying drawings, together with the detailed description, describe exemplary embodiments disclosed herein. The drawings are not to scale and the proportion of certain elements may be exaggerated for the purpose of illustration.

D. DETAILED DESCRIPTION

Figure 1:
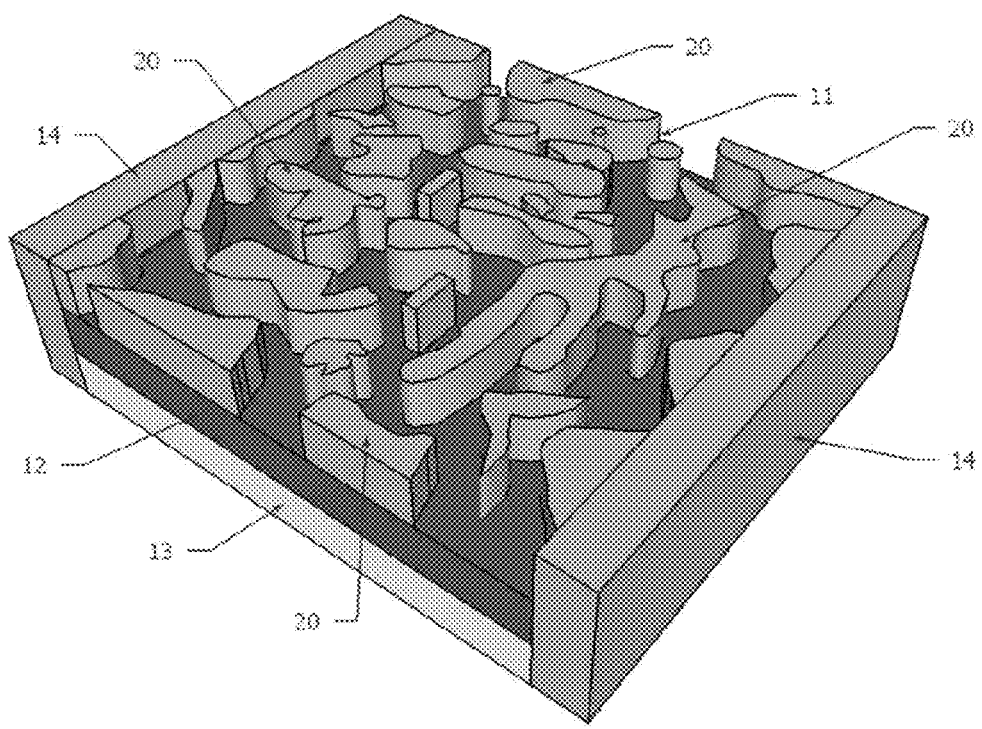
FIG. 1 is a perspective view of a gas detection film as described in accordance with some embodiments herein.

In the following detailed description, reference is made to the accompanying drawings, which form a part of this document. In the drawings, similar symbols typically identify similar components, unless the context dictates otherwise. The illustrative embodiments described in the detailed description, drawings, and claims are not meant to be limiting. Other embodiments may be used, and other changes may be made, without departing from the spirit or scope of the subject matter presented in this document. It will be readily understood that the aspects of the present disclosure, as generally described in this document, and illustrated in the Figures, can be arranged, substituted, combined, separated, and designed in a wide variety of different configurations, all of which are explicitly contemplated to be within the scope of this disclosure.

Percolation theory was developed to mathematically deal with disordered media, in which the disorder is defined by a random variation in the degree of connectivity. The main concept of percolation theory is the existence of a percolation threshold, defined in the following way. Suppose p is a parameter that defines the average degree of connectivity between various sub-units of some arbitrary system. When p=0, all sub-units are totally isolated from every other sub-unit. When p=1, all sub-units are connected to some maximum number of neighboring subunits. At this point, the system is connected from one side to the other, since there are paths that go completely across the system, linking one sub-unit to the next along the spanning cluster. Now suppose, starting at p=1, connections are randomly broken, so that p, the measure of average connectivity, decreases. The percolation threshold is that value of p, usually denoted pc, at which there is no longer an unbroken path from one side of the system to the other. Alternately, if we start out at p=0, and randomly create connections, so that p increases, pc is defined as the point at which a spanning cluster first appears. For p less than pc, only isolated, non-spanning clusters can exist. For p greater than pc, there is always a spanning cluster, although some isolated, non-spanning clusters can still be present. This percolation theory is applied to the gas detectors disclosed and described herein.

The analyte detector is adapted to detect an analyte in a fluid stream. By fluid stream it is meant either a gas stream or a liquid stream. The analyte or analytes can be in any form—solid, liquid, gas, ionized, etc., they may be particulate or dissolved.

In a liquid stream, the analyte may be suspended, dissolved, emulsified or otherwise present.

In a gas stream the analyte can similarly be suspended, dissolved, gaseous, particulate, or otherwise present. Exemplary gas streams include but are not limited to air, exhaust gases, stack gases, fumes, and other gas flows. Exemplary liquid streams include water flows, natural or man-made, alcohol, organic solvents, and oil. Exemplary organic solvents include but are not limited to pentane, cyclopentane, hexane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, formic acid, n-butanol, isopropanol, n-propanol, ethanol, methanol, acetic acid, water, etc. and combinations thereof.

Figure 2A:
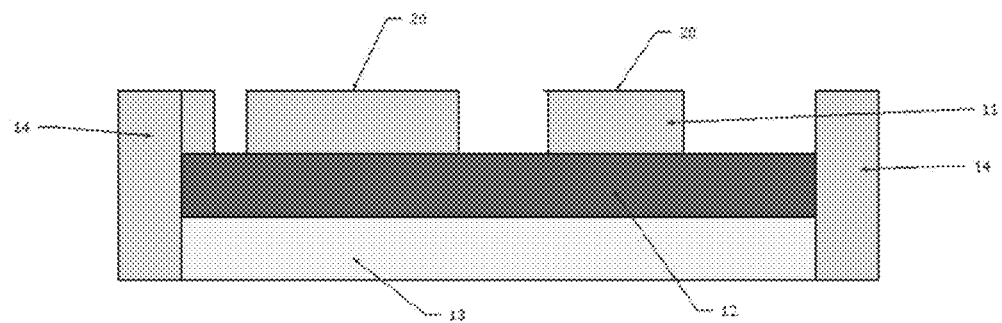
FIG. 2A is a cross-sectional view of a gas detection film in accordance with some embodiments herein prior to exposure to a detectable gas.
Figure 2B:
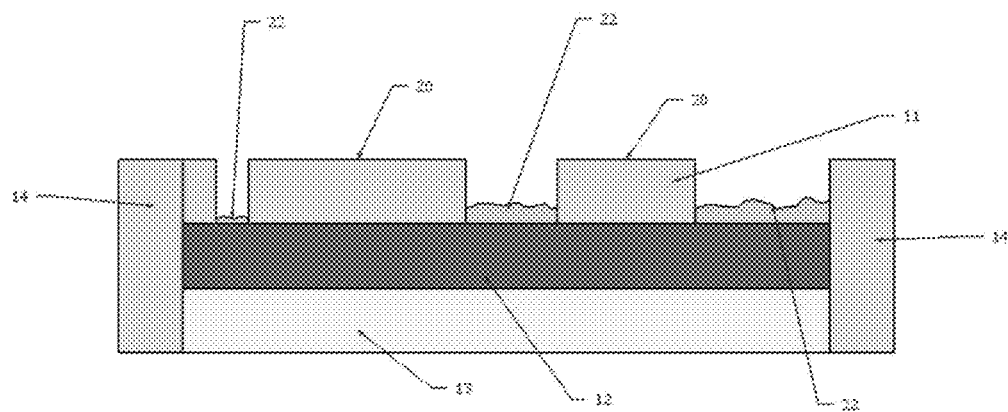
FIG. 2B is a cross-sectional view of a gas detection film in accordance with some embodiments herein after to exposure to a detectable gas.

Referring now to FIGS. 1 and 2A and 2B, in some embodiments, an analyte detection film 10 includes an insulating base layer 13, a conducting layer 11 including a plurality of conductive clusters 20 having a known degree of percolation below a percolation threshold; and a non-conductive reactant layer 12 between the insulating base layer and the conducting layer.

Some embodiments are directed to detecting or measuring a detectable gas concentration by detecting a jump in conductance of a gas detection film. In some embodiments, the analyte detection film may include an insulator base, a non-conducting insulator/semiconductor reactant layer in the middle and a near-percolation-threshold conducting layer having conducting clusters on top. The some conducting clusters may not be or may be barely connected to each other so long as the percolation threshold is not breached in the absence of the detectable analyte. Thus the analyte detection films are near, but below, the threshold of percolation in the absence of the detectable analyte. When the detectable analyte comes into contact or otherwise reacts with the analyte detection film, the number of contacts between the neighboring conducting clusters increases. This may be due to swelling of the conducting clusters due to the reaction of the analyte with the conducting clusters or due to interconnection via the formation of a conductive compound by reaction of the detectable analyte with the non-conductive reaction layer. In terms of percolation, the percolation threshold is breached. It should be appreciated that in some instances, the percolation threshold can be breached well before complete connectivity is reached (i.e. before p=1). This degree of connectivity or degree of percolation results in variations in conductance, resistivity, and/or current which can be used to determine the relative concentration of the detected analyte.

For example, in some embodiments where mercury vapor is the detectable analyte in a gas stream, conducting clusters may be deposited on a selenium sulfide surface in a near-percolation threshold concentration and arrangement. Because the conducting clusters are below the percolation threshold, they do not conduct across the detector. Also, spaces or gaps are present between the conductive clusters. The selenium sulfide non-conductive reactive layer is therefore exposed between conductive clusters. Upon contact with mercury vapor, selenium sulfide reacts with mercury to form mercury sulfide and mercury selenide, which is conducting. The mercury selenide bridges at least some neighboring conductive clusters and may result in a jump of conductance of the system. Selenium sulfide may react with mercury vapor even in low concentrations. Traditional methods such as visual detection of color change or measuring the electric properties of the entire sheet requires a long reaction time with less sensitivity relatively. On the other hand, introducing a percolation system, as disclosed in embodiments of this document, shortens reaction time and increases sensitivity of the reaction significantly.

Some embodiments herein provide for an analyte detection film including an insulating base layer, a conducting layer including a plurality of conductive clusters having a known degree of percolation below a percolation threshold; and a non-conductive reactant layer between the insulating base layer and the conducting layer. In some embodiments, the detectable gas may include mercury vapor, water vapor, formaldehyde or a combination thereof.

The insulating base layer may include any insulating material. In some embodiments, the insulating base layer may include glass, clay, quartz, alumina, feldspar, porcelain, silicon, siloxane, polymer, non-conducting metal oxides, polypropylene, fluorinated polyethylene, plastic, wax or a combination thereof. The non-conducting metal oxides may include iron oxide, aluminum oxide, silica, titanium oxide, antimony oxide, yttria, zirconia, or the like.

The conducting layer may include any conducting material. In some embodiments, the conducting layer may include graphite, graphene, conducting metals, doped semi-conductors, conductive polymers, copper, silver, aluminum, iron, iron nanopowders, carbon nanotubes, tantalum, tungsten, platinum, an alloy thereof or a combination thereof. The conducting metals may include magnesium, zinc, gold, silver, copper, aluminum, cobalt, brass, cadmium, chromium, iron, lead, tin, molybdenum, tungsten, nickel, platinum, or the like. Prior to exposure to a detectable gas, the conducting material is present in the conducting layers in amounts and arrangements such that the conducting layer is near its percolation threshold.

Conductive polymers may include melanins, such as polyacetylene, polypyrrole, and polyaniline, poly(p-phenylene vinylene), poly(3-alkylthiophenes), polythiophenes, poly (3,4-ethylenedioxythiophene) (PEDOT), poly(p-phenylene sulfide) (PPS), polycarbazoles, polyindoles, polyazepines, poly(acetylene)s (PAC), poly(fluorene)s, polyphenylenes, polypyrenes, polyazulenes, polynaphthalenes or the like.

In some embodiments, the known degree of percolation may be less than or about 50% below the percolation threshold. In some embodiments, the known degree of percolation may be less than or about 25% below the percolation threshold. In some embodiments, the known degree of percolation may be less than or about 10% below the percolation threshold. In some embodiments, the known degree of percolation may be less than or about 5% below the percolation threshold. In some embodiments, the known degree of percolation may be less than or about 1% below the percolation threshold. In some embodiments, the known degree of percolation may be within about 0.1% to about 50% below the percolation threshold. In some embodiments, the known degree of percolation may be within about 0.1% to about 25%, about 0.1% to about 10%, about 1% to about 50%, about 1% to about 25%, about 1% to about 10%, about 5% to about 50%, about 5% to about 25%, or about 5% to about 10% below the percolation threshold. Specific examples include about 0.1%, about 1%, about 5%, about 10%, about 5%, about 20%, about 5%, about 25%, about 30%, about 40%, or about 50% below the percolation threshold, or a range between any two of these values.

Figure 3:
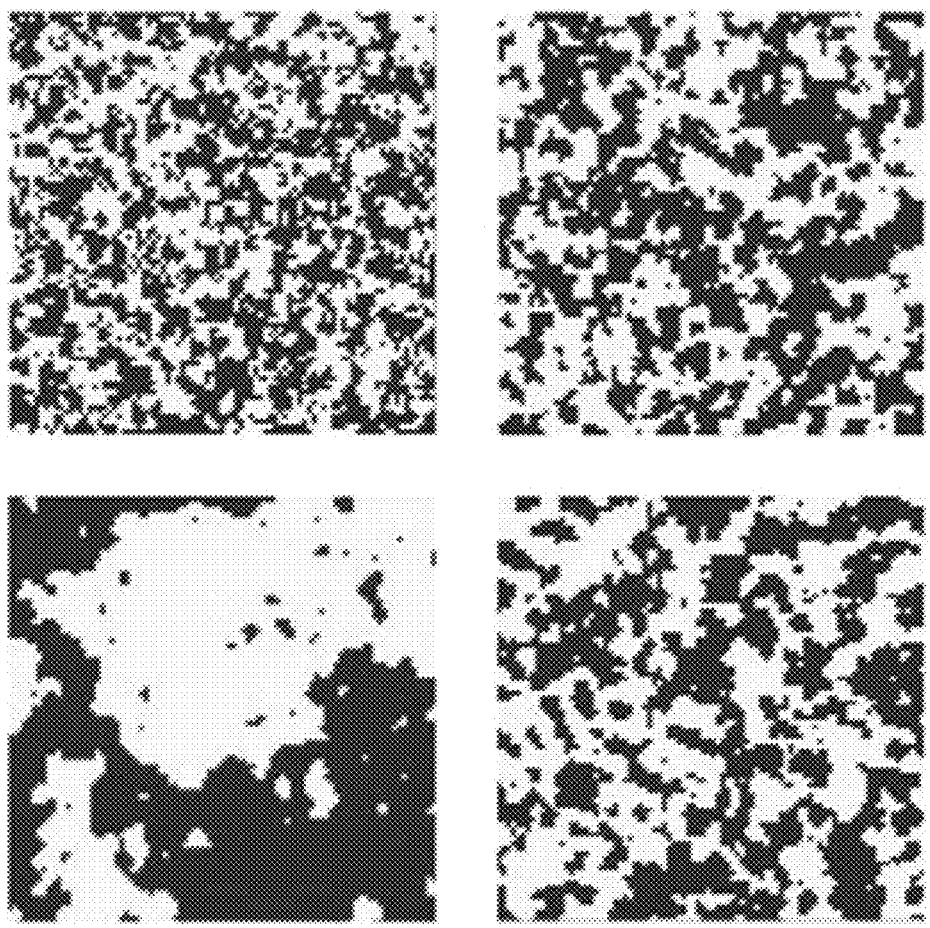
FIG. 3 shows a schematic illustration of exemplary percolation patterns.

In some embodiments, the plurality of conductive clusters may include a plurality of nanoclusters. As shown in FIG. 3, various percolation patterns may be possible. In some embodiments, each nanocluster may be less than about 100 nm apart from each other. In some embodiments, each nanocluster may be less than about 80 nm apart from each other. In some embodiments, each nanocluster may be less than about 50 nm apart from each other. In some embodiments, each nanocluster may be about 0.001 nm to about 100 nm apart from each other. In some embodiments, each nanocluster may be about 0.1 nm to about 100 nm apart, about 0.1 nm to about 80 nm apart, or about 0.1 nm to about 50 nm apart from each other. Specific examples may include about 0.001 nm, about 0.1 nm, about 0.5 nm, about 1 nm, about 10 nm, about 25 nm, about 50 nm, about 80 nm, about 95 nm, about 100 nm or a range between any two of these values. In some embodiments, the plurality of nanoclusters may have an average distance of less than about 100 nm apart from each other. In other embodiments, the plurality of nanoclusters may have an average distance of less than about 80 nm, less than about 50 nm or less than about 25 nm apart from each other. In some embodiments, the plurality of nanoclusters may have an average distance of about 0.1 nm to about 100 nm apart from each other. In some embodiments, the plurality of nanoclusters may have an average distance of about 0.1 nm to about 80 nm, about 0.1 nm to about 50 nm, about 0.1 nm to about 25 nm apart from each other. Specific examples include about 0.001 nm, about 0.1 nm, about 0.5 nm, about 1 nm, about 10 nm, about 25 nm, about 50 nm, about 80 nm, about 95 nm, about 100 nm or a range between any two of these values.

In some embodiments, the non-conductive reactant layer may include a material that is capable of reacting with the detectable analyte to increase surface conductivity causing the conducting layer to meet or exceed the percolation threshold. In some embodiments, the material may be non-conductive on its own but becomes conductive when it reacts with the detectable analyte. The material used in the non-conductive reactant layer may be chosen for detection of a specific analyte.

In some embodiments, the analyte may be a gas, a liquid, or a solid and maybe present in any form, dissolved, particulated, emulsified, etc. may include mercury vapor, water vapor, formaldehyde or a combination thereof. When the detectable analyte comes into contact with the gas detection film, it reacts with the non-conductive reactive layer 12 to yield a conductive compound 22 which together with at least some of the plurality of conductive clusters 20 of the conducting layer 11 meets or exceeds the percolation threshold thus creating a conductive pathway across the analyte detection film. In some embodiments, when the detectable analyte comes into contact with the analyte detection film, it may form an alloy with the conducting clusters causing them to swell and bridge the gap between the clusters. A jump in the conductance, resistivity or current of the analyte detection film may be detected or measured using electric contacts 14 on either side of the gas detection film. FIG. 2A shows a cross-sectional view of an analyte detection film prior to exposure to a detectable analyte. FIG. 2B shows a similar cross-sectional view after exposure to a detectable gas. It is readily seen that upon reaction of the non-conductive reactive layer 12 with the detectable analyte, a new, conductive compound 22 fills at least some of the gaps between the conductive clusters thereby completing a conductive path between the electrical contacts 13. The degree of formation of conductive paths, reduces the degree of percolation, and affects the conductance, resistivity, and/or current which can be used to determine the relative concentration of the detected analyte. Embodiments described in this document disclose a rapid alternative for measuring and detecting such analytes in comparison to the existing portable devices.

It should be noted that although this specification is drafted with specific reference to use of the detection film to detect an analyte, such as a detectable gas, in a gas stream, the technology is readily adaptable to use in fluids generally. That is, the technology can be adapted for use in any fluid stream whether it be gas or liquid. In particular, some detectors and methods of using them can be suited for use in fluids general, either gas or liquid. In other instances, the detectors and methods of using them will be particularly useful for gases. In yet other instances, the detectors and methods of using them will be particularly useful for liquids. Just as detectors used in gas streams can be used to detect specific gases in the gas stream, detectors for use in liquid streams can be adapted for measuring a detectable gas within the liquid stream, the gas may be entrapped, dissolved, or otherwise present in the liquid stream.

In some embodiments, the detectable gas may include mercury vapor. In some embodiments, the material that reacts with mercury vapor may include selenium sulfide, telluride sulfide, hydrogen sulfide, selenium chloride, selenium dioxide, selenium diiodide, selenium bromide, selenium difluoride, selenium hydride, sulfur dioxide, or a combination thereof. In some embodiments, the surface conductivity may be increased by forming a conducting compound selected from mercury sulfide, mercury selenide, or a combination thereof.

In some embodiments where mercury vapor is the detectable gas, the conducting layer may include a material that does not form an amalgam with mercury. In some embodiments, the conducting layer may include any conducting material. In some embodiments, the conducting layer may include a material that does form an amalgam with mercury.

Without wishing to be bound by theory, it is believed that for materials that do not form an amalgam with mercury, the non-conducting layer reacts with the mercury to form conducting products which causes a jump in conductance. It is believed that for materials that do form an amalgam with mercury, (1) the clusters may swell in size due to alloy formation thus meeting or exceeding the percolation threshold, and/or (2) some mercury may combine with the conducting clusters to form an alloy, the remaining mercury may still react with the non-conducting layer to activate percolation.

In some embodiments, where the detectable gas includes mercury vapor, the middle non-conducting layer may include materials that react with mercury vapor to form conducting products. For example, in some embodiments, selenium sulfide, which is non-conductive, may react with mercury vapor to form mercury sulfide and mercury selenide, which is conductive.

In some embodiments, where mercury vapor is the detectable gas, when the gas detection film is in contact with mercury vapor, areas of the non-conducting layer not covered by the conducting clusters may react with mercury vapor to form conducting products on the non-conducting layer, which bridge neighboring conducting clusters. In some embodiments, this causes overall conductance of the system to increase and the percolation threshold may be met or exceeded. In some embodiments, by detecting the occurrence, size, and timing of this conductance spike, the presence and concentration of mercury vapor may be identified. In some embodiments, conductance, resistance, current or a combination thereof may be measured.

In some embodiments, the detectable gas may include water vapor. In some embodiments, the material that reacts with water vapor may include a hydrogel. In some embodiments, the hydrogel may be selected from polyvinyl alcohol (PVA), polyacrylamide (PAAM), poly N-vinyl pyrrolidone (PNVP), polyhydroxyethyl methacrylate (PHEMA), polyethylene glycol (PEG), polyethylene oxide (PEO), polyethylene glycol monomethyl ether (PEGME), cellulose, dextrans, polysaccharides, agarose, acrylamide or derivatised acrylamide.

In some embodiments, upon contact with water vapor, the non-conducting hydrogel may become hydrated and thus become conducting, causing the gas detection film to meet or exceed the percolation threshold. In some embodiments, the reaction may be reversible. In some embodiments, upon drying, the sensor device may revert back to be non-conductive.

In some embodiments, the detectable gas may include formaldehyde. In some embodiments, the material that reacts with formaldehyde may include titanium oxide, tin oxide, zinc oxide, or a combination thereof. In some embodiments, the gas detection film may be doped with cadmium. Doping with cadmium may improve response time, sensitivity and selectivity of the film to formaldehyde.

In some embodiments, an analyte detection film can be incorporated into an analyte detection apparatus. As described above, in some embodiments, the analyte detection film includes an analyte detection film including an insulating base layer, a conducting layer including a plurality of conductive clusters having a known degree of percolation below a percolation threshold; and a non-conductive reactant layer between the insulating base layer and the conducting layer. In some embodiments, an analyte detection film is provided having a non-conducting layer that is capable of reacting with a detectable analyte, wherein the film is near the threshold of percolation and whereby the percolation threshold is breached when the analyte detection film is in the presence of or in contact with the detectable analyte. The analyte detection apparatus may further include a sensor in electrical communication with the analyte detection film for sensing a change in electrical conductivity or resistance in response to the presence of the detectable analyte in contact with the analyte detection film. In some embodiments, the percolation threshold is breached when the presence of the detectable analyte reacts with the analyte detection film to bridge the gap between neighboring conducting clusters on the conducting layer.

In some embodiments, the analyte detection film is a gas detection film and the detectable analyte is a detectable gas.

In some embodiments, the analyte detection film may be calibrated. The analyte detection film may be calibrated by measuring the exposure durations before conductance spikes under varying concentrations of the detectable analyte against homogenous samples of the analyte detection films.

In some embodiments, the analyte detection film may be a component of a signal reader device. In some embodiments, the analyte detection film may be a component of a disposable cartridge. The cartridges may be distinct detection systems which may allow monitoring in a harsh environment or at a distance. In some embodiments, the disposable nature of the cartridges may reduce exposure to poisonous analytes, such as mercury. In some embodiments, the analyte detection film may be electrically coupled to a sensor for measuring variation in conductivity, resistance, current or a combination thereof. In some embodiments, the signal reader device may be portable. In some embodiments, the signal reader device may be non-portable.

Methods of Preparing

Some embodiments provide for methods of preparing an analyte detection film, such as but not limited to gas detection film, including the steps of providing an insulating base layer; depositing onto the insulating base layer a non-conductive reactant layer that is capable of reacting with a detectable analyte, such as but not limited to a detectable gas, to increase conductivity of the analyte detection film; depositing onto the non-conductive reactant layer a conducting layer having a known degree of percolation below a percolation threshold.

In some embodiments, the conducting layer's plurality of conductive clusters may be formed by depositing conducting materials on the non-conducting layer under the right conditions. The conducting clusters may be deposited in an amount such that they have a known degree of percolation below a percolation threshold. For example, in some embodiments where mercury vapor is the detectable gas, forming the near-threshold percolation pattern may include depositing iron onto a selenium sulfide non-conducting layer. In some embodiments, the plurality of nanoclusters may spontaneously form or bead in order to reach the minimal surface free energy. In some embodiments, by varying reaction conditions, carbon nanotubes may be deposited on the non-conducting layer with controllable degrees of percolation.

In some embodiments, the method may further include electrically coupling the conducting layer to a sensor for sensing a change in electrical resistance in the conducting layer in response to the presence of the detectable analyte in contact with the analyte detection film, whereby the detectable analyte reacts with the non-conductive reactant layer to increase conductivity of the analyte detection film, thereby meeting or exceeding the percolation threshold. In some embodiments, the conducting layer meets or exceeds the percolation threshold when the analyte detection film is in contact with the detectable analyte.

Methods of Detection

Some embodiments relate to methods of detecting a detectable analyte, such as but not limited to a detectable gas, the method encompassing the steps of providing a fluid stream suspected of containing the detectable analyte; providing an analyte detection film having an insulating base layer, a conducting layer including a plurality of conducting clusters having a known degree of percolation that is below a percolation threshold, and a non-conductive reactant layer between the insulating base layer and the conducting layer; exposing the analyte detection film to the fluid stream; and measuring a conductance of the gas detection film, wherein an increase in conductance of the analyte detection film from a baseline level indicates the presence of the detectable analyte. As used herein, the term "detect" or "detecting" may include ascertain, measure, quantify, determine, identify, observe, see, establish, verify, or the like. In some embodiments, the non-conducting layer may be heated before, after or during the step of exposing the analyte detection film to a fluid stream including the detectable analyte. In some embodiments, the analyte detection film may be exposed to the fluid stream in the presence of oxygen. For example, a method of detecting formaldehyde may include heating the analyte detection film in order to react the analyte detection film with formaldehyde.

In some embodiments, the analyte detection film may be calibrated. In some embodiments, the method may further include calibrating the analyte detection film before determining the conductance of the analyte detection film. The analyte detection film may be calibrated by measuring the exposure durations before conductance spikes under varying concentrations of the detectable analyte against homogenous samples of the analyte detection films.

Kits

Some embodiments relate to kits for detecting a detectable analyte including an analyte detection film having an insulating base layer; a conducting layer including a plurality of conducting clusters having a known degree of percolation that is below a percolation threshold; and a non-conductive reactant layer between the insulating base layer and the conducting layer; instructions on how to use the analyte detection film. The kit may further include a chart for determining presence and concentration of the detectable analyte based on conductance of the analyte detection film. In some embodiments, the kit may include the detectable analyte in varying concentrations to calibrate the analyte detection film. In some embodiments, the kit may further include one or more disposable cartridges comprising the analyte detection film. In some embodiments, the kit may further include a notification device configured to provide a signal upon detection of the detectable analyte. In some embodiments, the signal may be any discernible signal. In some embodiments, the signal may be an auditory, haptic, gustatory, olfactory, visual, data, email, text, telepathic signal or a combination thereof. In some embodiments, the kit may further include a signal reader for use with the analyte detection film. In some embodiments, the signal reader allows a user to discern the change in conductance of the analyte detection film. In some embodiments, the signal reader may interpret the change in conductance and relay the presence, conductance or a combination thereof to the notification device. In some embodiments, the notification device may include a display. In some embodiments, the display may allow a user to determine the presence, concentration, or a combination thereof of the detectable analyte.

EXAMPLES

Example 1

Mercury Vapor Detection Film

A gas detection film for detecting mercury vapor will be made by depositing a non-conducting layer of selenium sulfide onto a glass insulating base layer and then depositing iron nanopowder (conducting clusters) onto the selenium sulfide coated glass in an amount that has a known degree of percolation below a percolation threshold. Upon contact with mercury vapor, selenium sulfide will react with the mercury to form mercury sulfide and mercury selenide, which is conducting, thus bridging neighboring clusters and resulting in a jump of conductance of the system. The conductance will be measured using electric contacts deposited on opposing sides of the gas detection film. The contacts will be connected to a circuit in order to measure conductivity, resistance, current or a combination thereof.

Example 2

Water Vapor Detection Film

A gas detection film for detecting water vapor gas will be made by depositing a hydrogel layer of polyvinylacrylamide onto a quartz surface. Carbon nanotubes will be then deposited onto the hydrogel layer in an amount that is a known degree of percolation below the percolation threshold. Upon contact with water vapor, the hydrogel will be hydrated and become conducting, causing a breach of percolation threshold. The reaction will also be reversible because upon drying, the polyvinylacrylamide will revert back to be non-conducting. The gas detection film will be electrically coupled to a sensor for sensing a change in electrical resistance in the conducting layer in response to the presence of water vapor in contact with the gas detection film.

Example 3

Formaldehyde Detection Film

A gas detection film for detecting formaldehyde gas will be made by depositing a non-conducting layer of titanium oxide onto a siloxane surface. Iron is then deposited on the titanium oxide layer in an amount with a known degree of percolation below the percolation threshold. When heated, $TiO_2$ will react with formaldehyde causing conductivity to increase. It is believed that carefully prepared $TiO_2$ will react with formaldehyde in the presence of oxygen. The gas detection film will be electrically coupled to a sensor for sensing a change in electrical resistance in the conducting layer in response to the presence of water vapor in contact with the gas detection film.

Example 4

Organic Solvent Detection Film

An analyte detection film for detecting an organic solvent in a liquid stream will be made by depositing a non-conducting layer of [selenium sulfide] onto a glass insulating base layer and then depositing [iron nanopowder] (conducting clusters) onto the [selenium sulfide] coated glass in an amount that has a known degree of percolation below a percolation threshold. Upon contact with organic solvent, [selenium sulfide] will react with the [solvent] to form [mercury sulfide] and [mercury selenide], which is conducting, thus bridging neighboring clusters and resulting in a jump of conductance of the system. The conductance will be measured using electric contacts deposited on opposing sides of the analyte detection film. The contacts will be connected to a circuit in order to measure conductivity, resistance, current or a combination thereof.

Example 5

Kit for Detecting Formaldehyde Gas

A kit for detecting formaldehyde gas will be prepared including a gas detection film having a siloxane base layer, conducting clusters of iron having a known degree of percolation that is below a percolation threshold, and a titanium oxide layer between the siloxane base layer and the conducting clusters of iron; and a set of instructions on how to use the gas detection film. The kit will also include a chart for determining presence and concentration of the formaldehyde gas based on conductance of the gas detection film. The kit may be calibrated using formaldehyde gas in varying concentrations. The kit may also include one or more disposable cartridges containing the gas detection film. The kit may also include a signal reader and/or a notification device for use with the gas detection film. The signal reader will interpret the change in conductance and relay the presence, conductance or a combination thereof to the notification device. The notification device will provide an audio signal when formaldehyde has been detected. The notification device may also display a warning or change color when formaldehyde has been detected.

Example 6

Kit for Detecting Water Vapor

A kit for detecting water vapor gas will be prepared including a gas detection film having a silicon base layer, conducting clusters of carbon nanotubes having a known degree of percolation that is below a percolation threshold, and a polyhydroxyethyl methacrylate layer between the silicon base layer and the conducting clusters of carbon nanotubes; and a set of instructions on how to use the gas detection film. The kit may also include a chart for determining presence and concentration of the water vapor based on conductance of the gas detection film. The kit may be calibrated using water vapor in varying concentrations. The kit may also include one or more disposable cartridges containing the gas detection film. The kit may also include a signal reader and a notification device for use with the gas detection film. The signal reader will interpret the change in conductance and relay the presence, conductance or a combination thereof to the notification device. The notification device will provide an audio signal when water vapor has been detected. The notification device may also display a warning or change color when water vapor has been detected.

Example 7

Kit for Detecting Mercury Vapor

A kit for detecting mercury vapor gas will be prepared including a gas detection film having a glass insulating base layer, conducting clusters of iron nanopowder having a known degree of percolation that is below a percolation threshold, and a selenium dioxide layer between the glass and the iron nanopowder; and a set of instructions on how to use the gas detection film. The kit may also include a chart for determining presence and concentration of the mercury vapor based on conductance of the gas detection film. The kit may be calibrated using mercury vapor in varying concentrations. The kit may also include one or more disposable cartridges containing the gas detection film. The kit may also include a signal reader and a notification device for use with the gas detection film. The signal reader will interpret the change in conductance and relay the presence, conductance or a combination thereof to the notification device. The notification device will provide an audio signal when mercury vapor has been detected. The notification device may also display a warning or change color when mercury vapor has been detected.

Example 8

Kit for Detecting Organic Solvents

A kit for detecting an organic solvent in a liquid stream will be prepared including an analyte detection film having a glass insulating base layer, conducting clusters of iron nanopowder having a known degree of percolation that is below a percolation threshold, and a [selenium dioxide] layer between the glass and the iron nanopowder; and a set of instructions on how to use the analyte detection film. The kit may also include a chart for determining presence and concentration of the organic solvent based on conductance of the analyte detection film. The kit may be calibrated using organic solvents in varying concentrations. The kit may also include one or more disposable cartridges containing the analyte detection film. The kit may also include a signal reader and a notification device for use with the analyte detection film. The signal reader will interpret the change in conductance and relay the presence, conductance or a combination thereof to the notification device. The notification device will provide an audio signal when mercury vapor has been detected. The notification device may also display a warning or change color when organic solvent(s) has been detected.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this document, will be apparent to those skilled in the art from the foregoing descriptions. Such modifications and variations are intended to fall within the scope of the appended claims. The present disclosure includes the full scope of equivalents to which the claims are entitled. It is to be understood that this disclosure is not limited to particular methods, reagents, compounds, compositions or biological systems, which can, of course, vary. It is also to be understood that the terminology used in this document is for the purpose of describing particular embodiments only, and is not intended to be limiting.

With respect to the use of substantially any plural and/or singular terms in this document, those having skill in the art can translate from the plural to the singular and/or from the singular to the plural as is appropriate to the context and/or application. The various singular/plural permutations may be expressly set forth in this document for sake of clarity.

It will be understood by those within the art that, in general, terms used in this document, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed in this document also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this document can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 layers refers to groups having 1, 2, or 3 layers. Similarly, a group having 1-5 layers refers to groups having 1, 2, 3, 4, or 5 layers, and so forth.

From the foregoing, it will be appreciated that various embodiments of the present disclosure have been described in this document for purposes of illustration, and that various modifications may be made without departing from the scope and spirit of the present disclosure. Accordingly, the various embodiments disclosed in this document are not intended to be limiting, with the true scope and spirit being indicated by the following claims.

The invention claimed is:

1. An analyte detection film comprising:
an insulating base layer;
a conducting layer including a plurality of conductive clusters having a known degree of percolation below a percolation threshold; and
a non-conductive reactant layer between the insulating base layer and the conducting layer.

2. The analyte detection film of claim 1, wherein the known degree of percolation is less than or about 10% below the percolation threshold.

3. The analyte detection film of claim 1, wherein the known degree of percolation is less than or about 5% below the percolation threshold.

4. The analyte detection film of claim 1, wherein the analyte detection film is capable of detecting a detectable gas selected from mercury vapor, water vapor, formaldehyde or a combination thereof.

5. The analyte detection film of claim 1, wherein the insulating base layer comprises glass, clay, quartz, alumina, feldspar, porcelain, silicon, non-conducting metal oxides, siloxane, polymer, polypropylene, fluorinated polyethylene, plastic, wax or a combination thereof.

6. The analyte detection film of claim 1, wherein the plurality of conductive clusters comprises a plurality of nano clusters.

7. The analyte detection film of claim 6, wherein each nanocluster is about 0.1 nm to about 100 nm apart from each other.

8. The analyte detection film of claim 6, wherein the plurality of nanoclusters have an average distance of about 0.1 nm to about 100 nm apart from each other.

9. The analyte detection film of claim 1, wherein the conducting layer comprises graphite, graphene, conducting metals, doped semi-conductors, conductive polymers, copper, silver, aluminum, iron, iron nano-powders, carbon nanotubes, tantalum, tungsten, platinum, an alloy thereof or a combination thereof.

10. The analyte detection film of claim 1, wherein the conducting layer meets or exceeds the percolation threshold when the analyte detection film is in contact with a detectable analyte.

11. The analyte detection film of claim 10, wherein the non-conductive reactant layer comprises a material that is capable of reacting with the detectable analyte to increase surface conductivity causing the conducting layer to meet or exceed the percolation threshold.

12. The analyte detection film of claim 11, wherein the detectable analyte is a detectable analyte comprising mercury vapor.

13. The analyte detection film of claim 12, wherein the material that reacts with mercury vapor comprises selenium sulfide, telluride sulfide, hydrogen sulfide, selenium chloride, selenium dioxide, selenium diiodide, selenium bromide, selenium difluoride, selenium hydride, sulfur dioxide, or a combination thereof.

14. The analyte detection film of claim 12, wherein the surface conductivity is increased by forming a conducting compound selected from mercury sulfide, mercury selenide, or a combination thereof.

15. The analyte detection film of claim 11, wherein the detectable analyte is a detectable gas comprising water vapor.

16. The analyte detection film of claim 15, wherein the material that reacts with the detectable analyte comprises a hydrogel.

17. The analyte detection film of claim 16, wherein the hydrogel is selected from polyvinyl alcohol (PVA), polyacrylamide (PAAM), poly N-vinyl pyrrolidone (PNVP), polyhydroxyethyl methacrylate (PHEMA), polyethylene glycol (PEG), polyethylene oxide (PEO), polyethylene glycol monomethyl ether (PEGME), cellulose, dextrans, polysaccharides, agarose, acrylamide or derivatised acrylamide.

18. The analyte detection film of claim 11, wherein the detectable analyte is a detectable gas comprising formaldehyde.

19. The analyte detection film of claim 18, wherein the material that reacts with formaldehyde comprises titanium oxide, tin oxide, zinc oxide, or a combination thereof.

20. The analyte detection film of claim 1, wherein the analyte detection film is a component of a signal reader device.

21. The analyte detection film of claim 1, wherein the analyte detection film is a component of a disposable cartridge.

22. The analyte detection film of claim 1, wherein the analyte detection film is electrically coupled to a sensor for measuring variation in conductivity, resistance, current or a combination thereof.

* * * * *